(12) United States Patent (10) Patent No.: US 8,052,683 B2
Podmore et al. (45) Date of Patent: Nov. 8, 2011

(54) DEVICE FOR ABLATION AND VISUALIZATION

(75) Inventors: Jonathan L. Podmore, San Carlos, CA (US); Michael Holzbaur, East Palo Alto, CA (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 0 days.

(21) Appl. No.: 11/642,923

(22) Filed: Dec. 21, 2006

(65) Prior Publication Data

US 2007/0299437 A1 Dec. 27, 2007

Related U.S. Application Data

(60) Provisional application No. 60/815,880, filed on Jun. 23, 2006, provisional application No. 60/815,852, filed on Jun. 23, 2006, provisional application No. 60/815,853, filed on Jun. 23, 2006, provisional application No. 60/815,881, filed on Jun. 23, 2006, provisional application No. 60/815,882, filed on Jun. 23, 2006.

(51) Int. Cl.
*A61B 18/14* (2006.01)
(52) U.S. Cl. .............................. 606/46; 606/41; 600/104
(58) Field of Classification Search ................ 606/41, 606/45–50; 600/104–110
See application file for complete search history.

(56) References Cited

U.S. PATENT DOCUMENTS

| 2,532,043 | A | * | 11/1950 | Wallace | 600/105 |
| 4,068,667 | A | * | 1/1978 | Iglesias | 606/46 |
| 4,374,517 | A | * | 2/1983 | Hagiwara | 600/104 |
| 4,422,457 | A | * | 12/1983 | Hattori | 606/2 |
| 5,056,503 | A | * | 10/1991 | Nagasaki et al. | 600/110 |
| 5,197,963 | A | * | 3/1993 | Parins | 606/46 |
| 5,275,151 | A | * | 1/1994 | Shockey et al. | 600/108 |
| 5,492,131 | A | | 2/1996 | Galel | |
| 5,611,777 | A | | 3/1997 | Bowden et al. | |
| 5,667,473 | A | * | 9/1997 | Finn et al. | 600/104 |

(Continued)

FOREIGN PATENT DOCUMENTS

EP 1639936 3/2006

OTHER PUBLICATIONS

International Search Report and Written Opinion for PCT/US07/71771 filed Jun. 21, 2007, date Apr. 30, 2008.

*Primary Examiner* — Michael Peffley
(74) *Attorney, Agent, or Firm* — Wiley Rein LLP

(57) ABSTRACT

An ablation and visualization device includes a shaft, at least one ablation element coupled to the distal end of the shaft, and a scope coupled to the shaft proximate the distal end. The scope may be a fiber optic endoscope, an infrared sensor, or an ultrasound sensor, and may be coupled to an output device to display imagery collected by the scope. The scope includes at least one aperture, which may be movable. An optical element, such as a lens or filter, may be positioned over the aperture. The scope may be positioned laterally relative to the ablation elements or in a plane substantially parallel to and spaced apart from the ablation elements. The scope may be positioned with the aperture positioned distally or proximally relative to the ablation elements. The scope may be slidably or rotatably coupled to the shaft.

32 Claims, 8 Drawing Sheets

U.S. PATENT DOCUMENTS

| | | | |
|---|---|---|---|
| 5,674,184 A * | 10/1997 | Hassler, Jr. | 600/176 |
| 5,849,011 A * | 12/1998 | Jones et al. | 606/47 |
| 5,873,877 A * | 2/1999 | McGaffigan et al. | 606/41 |
| 5,935,102 A | 8/1999 | Bowden et al. | |
| 5,935,125 A * | 8/1999 | Zupkas | 606/46 |
| 6,071,233 A | 6/2000 | Ishikawa et al. | |
| 6,071,274 A | 6/2000 | Thompson et al. | |
| 6,071,279 A | 6/2000 | Whayne et al. | |
| 6,086,583 A * | 7/2000 | Ouchi | 606/41 |
| 6,106,521 A * | 8/2000 | Blewett et al. | 606/41 |
| 6,198,974 B1 | 3/2001 | Webster, Jr. | |
| 6,210,407 B1 | 4/2001 | Webster | |
| 6,314,962 B1 | 11/2001 | Vaska et al. | |
| 6,314,963 B1 | 11/2001 | Vaska et al. | |
| 6,330,473 B1 | 12/2001 | Swanson et al. | |
| 6,394,949 B1 * | 5/2002 | Crowley et al. | 600/127 |
| 6,402,746 B1 | 6/2002 | Whayne et al. | |
| 6,454,758 B1 | 9/2002 | Thompson et al. | |
| 6,551,315 B2 * | 4/2003 | Kortenbach et al. | 606/46 |
| 6,689,128 B2 | 2/2004 | Sliwa, Jr. et al. | |
| 6,689,130 B2 * | 2/2004 | Arai et al. | 606/46 |
| 6,701,931 B2 | 3/2004 | Sliwa, Jr. et al. | |
| 6,726,684 B1 * | 4/2004 | Woloszko et al. | 606/32 |
| 6,840,936 B2 * | 1/2005 | Sliwa et al. | 606/41 |
| 6,858,003 B2 | 2/2005 | Evans et al. | |
| 6,858,026 B2 | 2/2005 | Sliwa, Jr. et al. | |
| 6,923,806 B2 | 8/2005 | Hooven et al. | |
| 6,971,394 B2 | 12/2005 | Sliwa, Jr. et al. | |
| 7,025,766 B2 | 4/2006 | Whayne et al. | |
| 7,052,493 B2 | 5/2006 | Vaska et al. | |
| 2003/0181900 A1 | 9/2003 | Long | |
| 2005/0159798 A1 | 7/2005 | Graumann et al. | |

\* cited by examiner

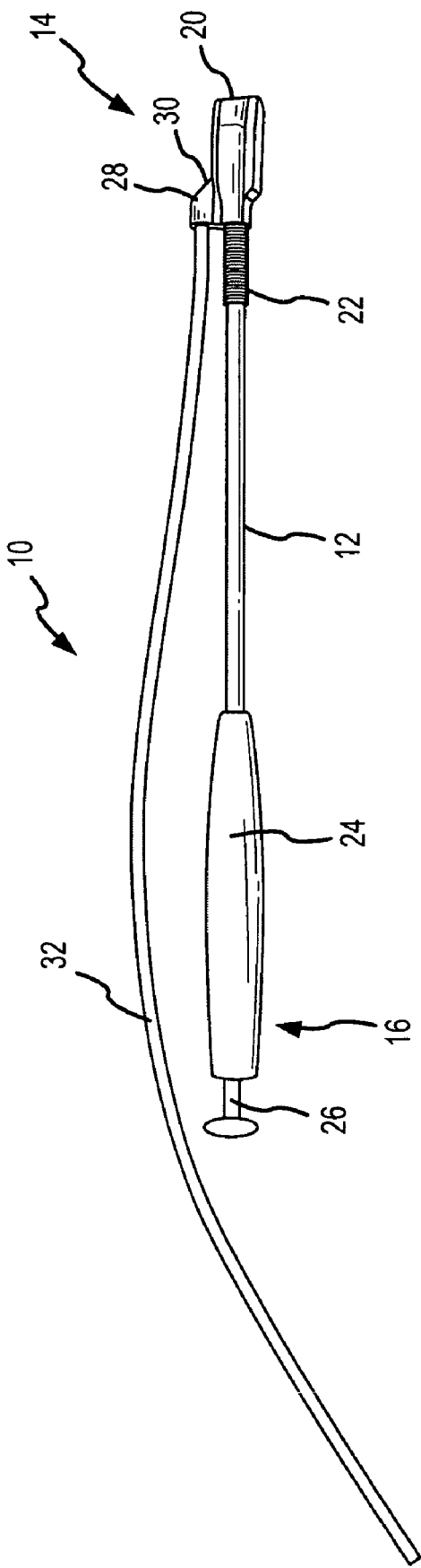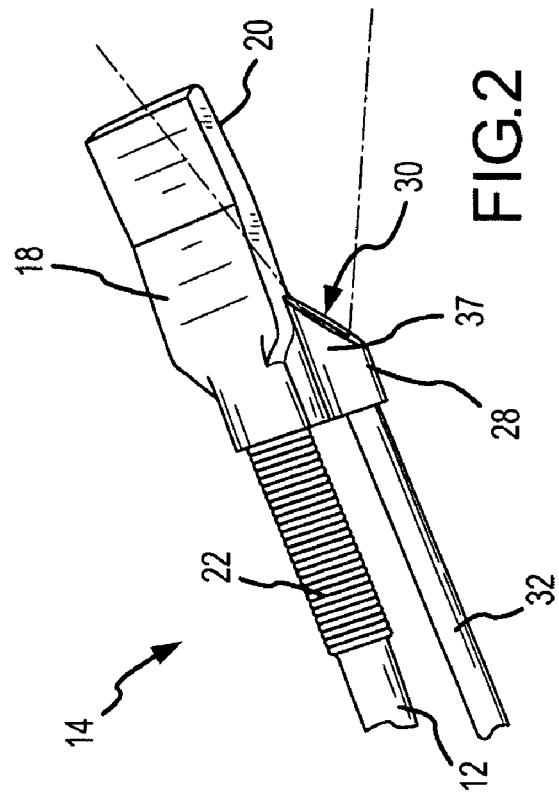

DEVICE FOR ABLATION AND VISUALIZATION

CROSS-REFERENCE TO RELATED APPLICATIONS

This application claims the benefit of U.S. provisional application No. 60/815,880, filed 23 Jun. 2006, which is hereby incorporated by reference as though fully set forth herein.

This application is related to U.S. provisional application No. 60/815,852, U.S. provisional application No. 60/815,853, U.S. provisional application No. 60/815,881, and U.S. provisional application No. 60/815,882, all filed 23 Jun. 2006. All of the foregoing applications are hereby incorporated by reference as though fully set forth herein.

BACKGROUND OF THE INVENTION a. Field of the Invention

The instant invention relates to the treatment of atrial fibrillation. In particular, the instant invention relates to devices and methods for visualizing target tissues during epicardial mapping and ablation procedures.

b. Background Art

It is well known that atrial fibrillation results from disorganized electrical activity in the heart muscle (the myocardium). The surgical maze procedure has been developed for treating atrial fibrillation, and involves the creation of a series of surgical incisions through the atrial myocardium in a preselected pattern so as to create conductive corridors of viable tissue bounded by scar tissue.

As an alternative to the surgical incisions of the maze procedure, transmural ablations of the heart may be used. Such ablations may be performed either from within the chambers of the heart (endocardial ablation), using endovascular devices (e.g., catheters) introduced through arteries or veins, or from outside the heart (epicardial ablation) using devices introduced into the patient's chest. Various ablation techniques may be used, including, but not limited to, cryogenic ablation, radio frequency (RF) ablation, laser ablation, ultrasonic ablation, and microwave ablation. The ablation devices are used to create elongated transmural lesions—that is, lesions extending through a sufficient thickness of the myocardium to block electrical conduction—forming the boundaries of the conductive corridors in the atrial myocardium. Perhaps most advantageous about the use of transmural ablation rather than surgical incision is the ability to perform ablation procedures without first establishing cardiopulmonary bypass (CPB).

In performing the maze procedure and its variants, whether using ablation or surgical incisions, it is generally considered most efficacious to include a transmural incision or lesion isolating the pulmonary veins from the surrounding myocardium. The pulmonary veins connect the lungs to the left atrium of the heart, joining the left atrial wall on the posterior side of the heart. Such procedures have been found to offer 57% to 70% success without antiarrhythmic drugs. However, they are also associated with a 20% to 60% recurrence rate as the result of lesion recovery, non-pulmonary vein foci of the arrhythmia, or the need for further tissue modifications.

Previous surgical and catheter-based approaches have demonstrated that linear left atrial (LA) lesions were successful in treating atrial fibrillation when complete block was achieved. One such technique involves linear ablation at the mitral isthmus, which is defined as extending from the lateral mitral annulus to the ostium of the left inferior pulmonary vein (LIPV). Studies have shown that catheter ablation of the mitral isthmus, in combination with pulmonary vein (PV) isolation, consistently results in demonstrable conduction block and is associated with a high cure rate for paroxysmal atrial fibrillation.

Producing precise lesions at these locations presents significant obstacles for the physician performing endocardial ablations for several reasons. First, while many of the lesions created in the maze procedure can be created from within the right atrium, the pulmonary venous lesions must be created in the left atrium, requiring either a separate atrial access point or a transseptal puncture from the right atrium. Second, the elongated and flexible endovascular ablation devices are difficult to manipulate into the complicated geometries required for forming the pulmonary venous lesions. It is also difficult to maintain proper positioning of the ablation device against the wall of a beating heart. Furthermore, visualization of endocardial anatomy and endovascular devices is often inadequate, such that knowing the precise position of an endovascular device can be difficult, potentially resulting in misplaced lesions.

Epicardial ablation devices and methods useful for creating transmural lesions for the treatment of atrial fibrillation have been described in U.S. Pat. No. 7,052,493 to Vaska et al. ("Vaska") and U.S. Pat. No. 6,971,394 to Sliwa et al. ("Sliwa"), both of which are hereby expressly incorporated by reference as though fully set forth herein. Sliwa describes a method of forming a transmural lesion in a wall of the heart adjacent to the pulmonary veins by placing an ablation device through a thoracic incision, and then through a pericardial penetration, so that the ablation device is disposed in contact with an epicardial surface of the heart. The ablation device includes a locating device, such as a catch, a branch, or a notch, near the working end of the catheter that is configured to engage one or more of the pulmonary veins or another nearby anatomical structure (e.g., a pericardial reflection, the inferior vena cava, the superior vena cava, the aorta, the left or right atrial appendage) in order to position the working end of the catheter adjacent to the pulmonary veins.

Precise placement of the ablating elements on the epicardial surface is critical to the efficacy of PV isolation and mitral isthmus ablations. The anatomic relationship of tissues other than the heart is also a very important consideration. For example, due to the proximity of the esophagus to the posterior left atrium of the heart, great care must be taken to prevent damage to the esophagus during an ablation procedure, as atrioesophageal fistulas have been reported as a complication following catheter ablation for atrial fibrillation. Reliance on non-visual locating devices, however, requires a very high degree of physician skill and experience, and may hinder such precise placement.

BRIEF SUMMARY OF THE INVENTION

It is therefore desirable to provide a device permitting the physician to directly see the anatomical features of the heart necessary to confirm correct placement of ablation devices in an ablation procedure.

It is also desirable to provide a device permitting the physician to visually verify the relationship of other tissues and organs to the ablation device and the tissue to be ablated.

According to a first embodiment of the invention, a device for ablating tissue includes: a shaft having a distal end; at least one ablation element coupled to the distal end of the shaft; and a scope coupled to the shaft proximate the distal end, the scope including at least one image collecting aperture. The scope may be a fiber optic endoscope, an infrared sensor, or an ultrasound sensor, and may optionally be coupled to an output device configured to visually display imagery collected by the scope through the image collecting aperture. At least one optical element may be positioned over the at least one image collecting aperture. In some embodiments of the invention, the scope includes a plurality of image collecting apertures, one or more of which may be movable.

The scope may be positioned laterally relative to the at least one ablation element or in a plane substantially parallel to and spaced apart from a plane in which the at least one ablation element is located. Further, the scope may be positioned with the at least one aperture positioned distally or proximally relative to the at least one ablation element, and may be positioned such that a field of view of the scope includes at least a portion of the at least one ablation element. Optionally, the scope may be slidably or rotatably coupled to the shaft. Alternatively, the scope may be integrated with the shaft.

A cap, which may be substantially transparent, may be coupled, optionally removably coupled, to the distal end of the shaft, and the scope may be coupled, optionally removably coupled, to the shaft via the cap. The at least one optical element, such as a lens or filter, may be integrated into the cap.

According to another embodiment of the invention, an ablation and visualization device includes: a shaft having a distal end and a proximal end; at least two ablation elements located on the distal end of the shaft; and a scope coupled to the distal end of the shaft, the scope including at least one image collecting aperture, which may be movable via a swivel assembly. Optionally, the device includes an optical element positioned over the image collecting aperture to alter a field of view of the scope. The optical element may be a lens or a filter. The scope may be integrated with the distal end of the shaft, directly coupled to the distal end of the shaft, or coupled to a substantially transparent cap that is coupled to the distal end of the shaft.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 1 illustrates an ablation and visualization device.

FIG. 2 is an enlarged view of the distal end of the ablation and visualization device illustrated in FIG. 1.

DETAILED DESCRIPTION OF THE INVENTION

Figure 3:
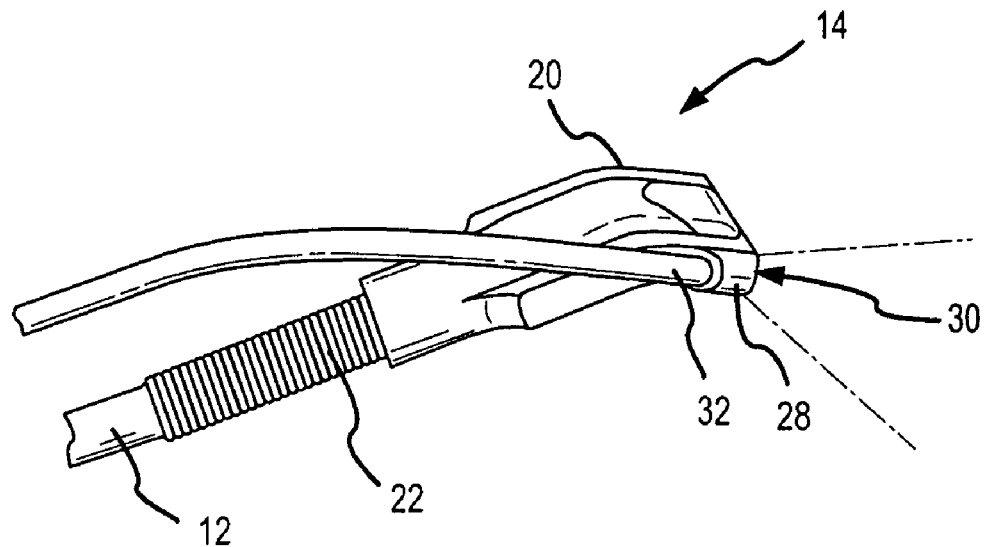
FIG. 3 illustrates the distal end of an ablation and visualization device with the scope positioned in a lateral and distal configuration.

FIG. 1 illustrates an ablation and visualization device 10 according to a first embodiment of the invention. Ablation and visualization device 10 generally includes a shaft 12 having a distal end 14 (illustrated in enlarged view in FIG. 2) and a proximal end 16.

At least one ablation element 18 is provided on distal end 14. The embodiment of device 10 illustrated includes two ablation elements 18, though one of skill in the art will appreciate that the precise number of ablation elements 18 may vary with the particular application of ablation and visualization device 10. One of skill in the art will further appreciate that ablation elements 18 may be any suitable element, such as an ultrasound ablation element, an RF ablation element, or a laser ablation element. The ablation elements 18 may be fixed relative to one another or may be flexibly or malleably interconnected so as to permit adjustment of their relative orientation or position. In some embodiments of device 10, ablation elements 18 are substantially enclosed within a housing 20.

Preferably, shaft 12 is relatively rigid, while distal end 14 is preferably articulable into a variety of positions relative to shaft 12, permitting a user to adjust ablation elements 18 for both the angle of introduction of device 10 into a patient's body and the orientation of the target surface. Thus, distal end 14 may incorporate a stacked coil 22 that will retain a deformed shape when deformed by a user. Stacked coil 22 may be enclosed within a sheath. It should be understood, however, that distal end 14 may be made articulable in any fashion without departing from the spirit and scope of the present invention. In addition, the use of a steerable shaft 12 rather than a relatively rigid shaft 12 is regarded as within the scope of the invention.

A handle 24 may be included at proximal end 16 of shaft 12. Device 10 may also include a connector 26 at proximal end 16. Connector 26 may be configured to couple device 10 to a fluid delivery and withdrawal mechanism, a suction system, a control system, a data collection system, an ablation energy delivery system, and any combination thereof. Handle 24 may include actuators or other control mechanisms for any of the systems to which device 10 is coupled via connector 26 (e.g., a switch to activate or deactivate the ablation energy system). Preferably, connector 26 includes an EEPROM that permits device 10 to be used only for a limited amount of time, such as about six hours, once connected to an ablation system.

A scope 28 is attached to or integrated with shaft 12 at or near distal end 14. Scope 28 collects imagery from within the patient via an aperture 30, which may then be output on a monitor or display. The imagery provides visual confirmation of both the anatomical surroundings and the relative orientation of device 10. The physician can thus utilize the imagery as a visual aid in properly positioning ablation elements 18 for the creation of ablation lesions. In addition, the imagery aids the physician in identifying, locating, and avoiding non-target tissues, such as esophageal tissue, thereby substantially reducing the likelihood of collateral damage to surrounding organs and tissue during an ablation procedure.

In some embodiments of the invention, scope 28 is a fiber optic endoscope that transmits images over an optical fiber 32 to a display device (not shown). Optical fiber 32 may be connected directly to aperture 30. It should be understood, however, that other scopes 28 are also contemplated, including, for example, ultrasound sensors and infrared sensors. Thus, the term "scope" is intended to encompass all image capture devices, visualization devices, cameras, sensors, and other similar devices capable of capturing and transmitting imagery, provided the device is small enough to be suitable for surgical use, the term "aperture" is intended to encompass the terminal ends of all such devices, and the term "imagery" is intended to encompass all imagery collected or captured by scope 28, regardless of its form (e.g., visible light, infrared energy) or output.

Scope 28 may be positioned in a number of configurations depending on the particular application of device 10. FIGS. 1 and 2 illustrate scope 28 positioned laterally relative to ablation elements 18. That is, scope 28 is positioned in substantially the same plane as ablation elements 18. In addition, scope 28 is positioned with aperture 30 located proximally relative to ablation elements 18 (i.e., aperture 30 is positioned towards handle 24). At least a portion of ablation elements 18 may therefore be in the field of view of scope 28, which provides the user of device 10 with a reference point for determining the spatial relationship between device 10, the tissue to be ablated, and any surrounding non-target tissue or anatomical structures. This configuration is particularly desirable where access is extremely limited and the user wishes to identify ablation target locations, such as the mitral annulus line.

Figure 4:
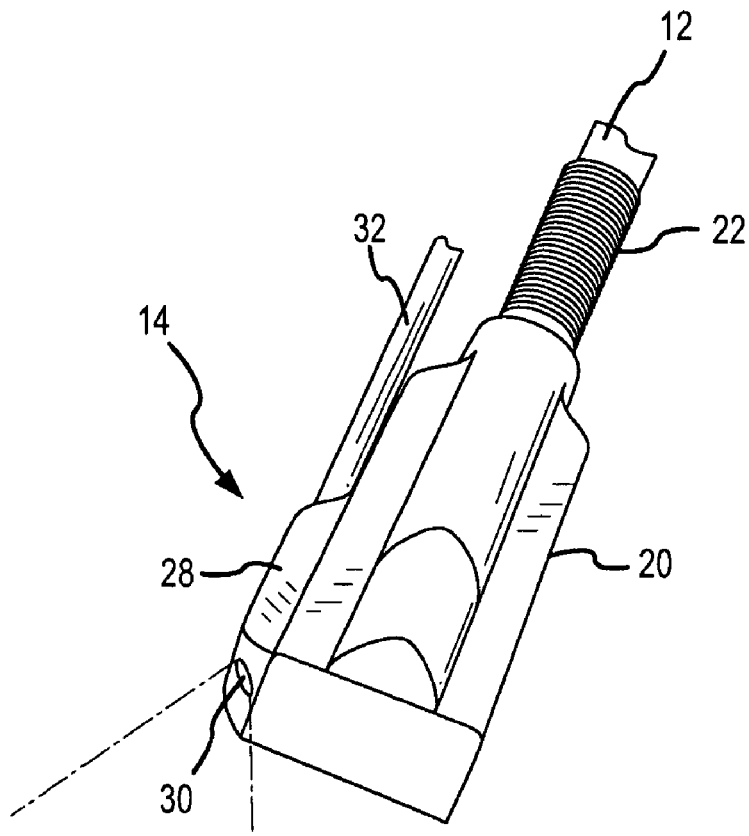
FIG. 4 also illustrates the scope positioned in a lateral and distal configuration.

Another embodiment of device 10 is illustrated in FIGS. 3 and 4. Scope 28 is once again positioned laterally relative to ablation elements 18. However, scope 28 is positioned more distally relative to the embodiment illustrated in FIGS. 1 and 2. This configuration is particularly desirable where the user desires the lesion to be created near or against a structure, such as a pulmonary vein. It should be understood that, though FIGS. 3 and 4 illustrate aperture 30 positioned substantially parallel to the most distal ablating element 18, aperture 30 could equally well be positioned more distally than the most distal ablating element 18 without departing from the spirit and scope of the present invention.

Figure 5:
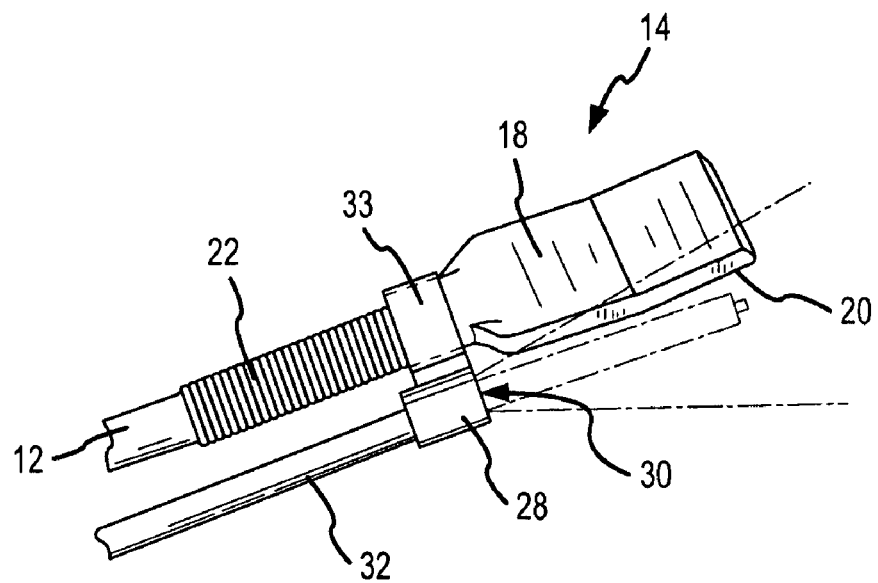
FIG. 5 depicts the distal end of an ablation and visualization device with the scope slidably coupled to the shaft in a lateral configuration.

In still another embodiment of device 10 illustrated in FIG. 5, scope 28 is slidably coupled to shaft 12 via a collar 33. In the embodiment illustrated in FIG. 5, scope 28 is positioned laterally relative to ablation elements 18. Collar 33 permits scope 28 to slide distally and proximally relative to shaft 12 such that scope 28 can be positioned at two or more points along shaft 12. For example, scope 28 may be initially positioned proximally as shown in solid lines in FIG. 5 in order to provide a reference for the spatial relationship of device 10 relative to the tissue to be ablated and neighboring anatomical features. The physician may then advance scope 28 distally through collar 33 into the position shown in phantom in order to improve viewing of features located distally to device 10, for example to verify that ablation elements 18 are positioned over the mitral isthmus. Thus, in the embodiment illustrated in FIG. 5, scope 28 can be adjusted such that aperture 30 may be positioned both distally and proximally relative to ablation elements 18. Further, collar 33 may be rotatably coupled to shaft 12 such that scope 28 may be revolved about shaft 28 and positioned in a plurality of planes parallel to and spaced from the plane of ablation elements 18.

Figure 6:
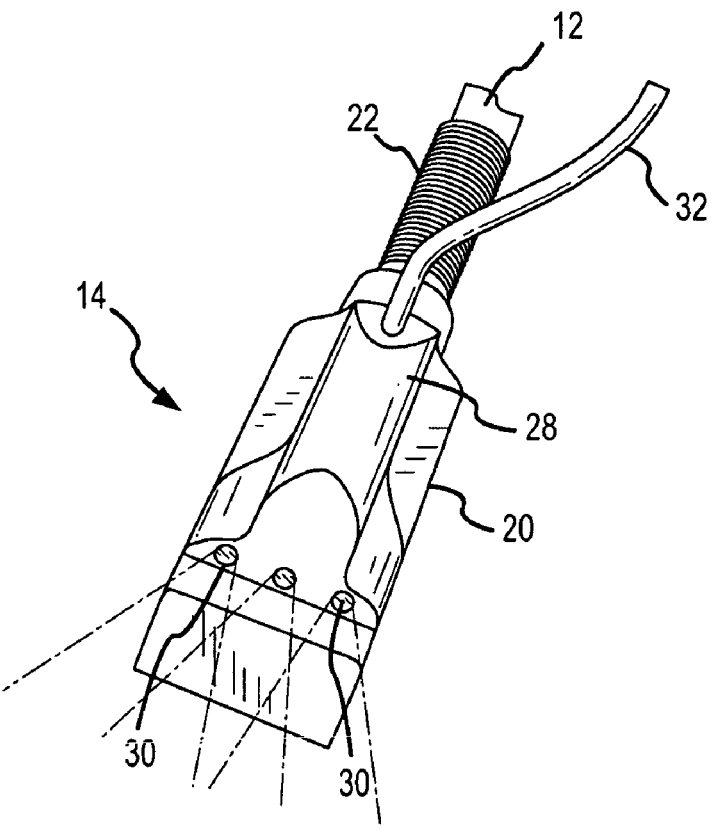
FIG. 6 shows the distal end of an ablation and visualization device with a scope having multiple viewing apertures.

FIG. 6 illustrates an embodiment of device 10 where scope 28 includes multiple apertures 30. Apertures 30 may be pointed in different directions, allowing the physician additional fields of view in front of, above, and to the side of ablation elements 18. Further, FIG. 6 illustrates scope 28 top-mounted on device 10. That is, rather than positioning scope 28 laterally to ablation elements 18, scope 28 is positioned in a plane substantially parallel to and spaced from the plane of ablation elements 18. The imagery captured by apertures 30 may be displayed side-by-side, for example in a split-screen or multiple-monitor configuration. Alternatively, the physician may elect one aperture 30 for output, switching between apertures 30 as desired.

Figure 7:
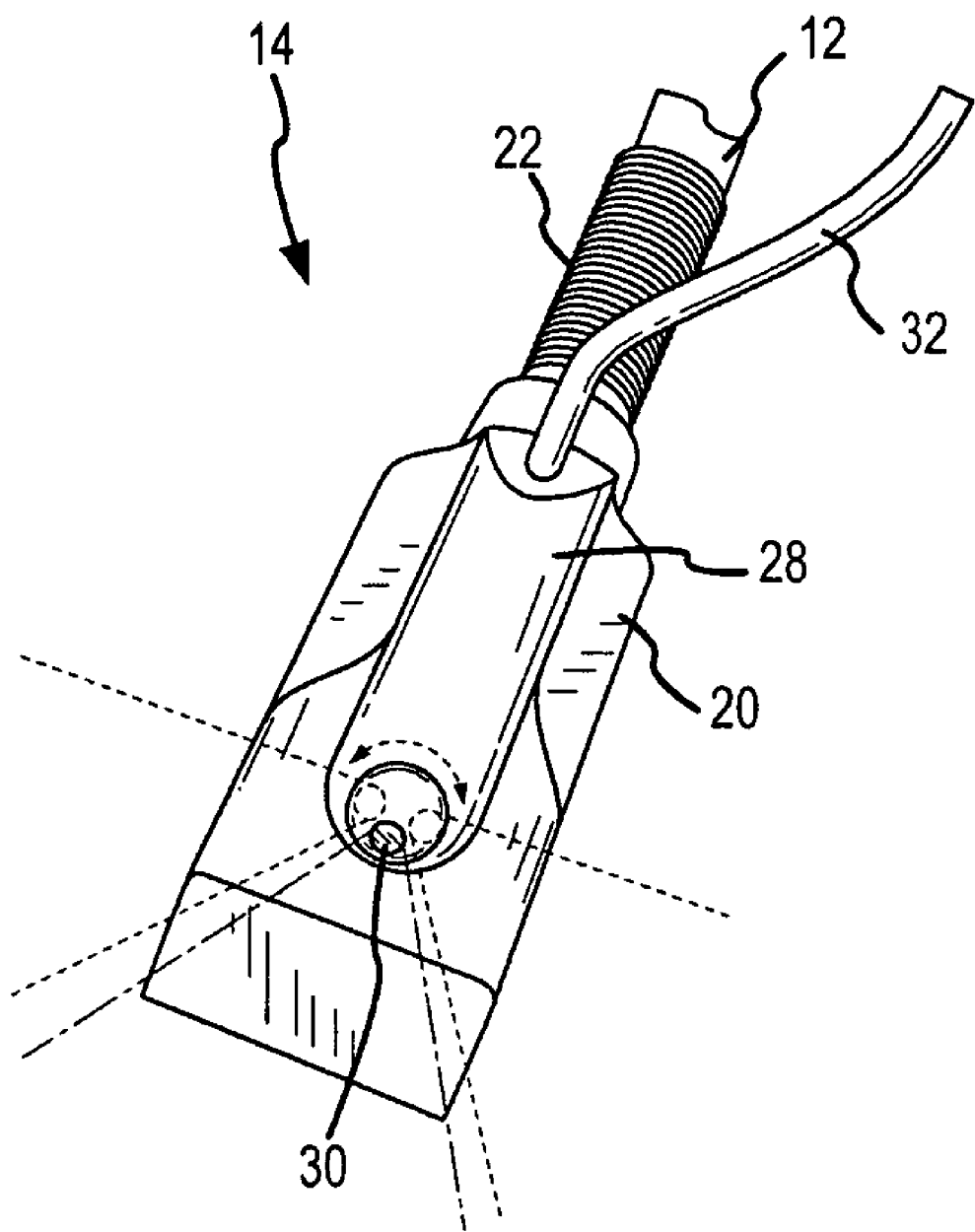
FIG. 7 illustrates the distal end of an ablation and visualization device with a scope having a movable viewing aperture.

Yet another embodiment of device 10 is depicted in FIG. 7. In FIG. 7, scope 28 is positioned in a plane substantially parallel to and spaced apart from the plane of ablation elements 18. Scope 28 includes a single, movable aperture 30. Use of a movable aperture 30 permits the physician to direct the field of view in a desired direction and to adjust the field of view during the procedure. Aperture 30 may be mounted on a swivel assembly, such as a ball-and-socket joint, or otherwise articulated. Control for the movable aperture 30 may be provided via one or more actuators incorporated into handle 24.

Figure 8:
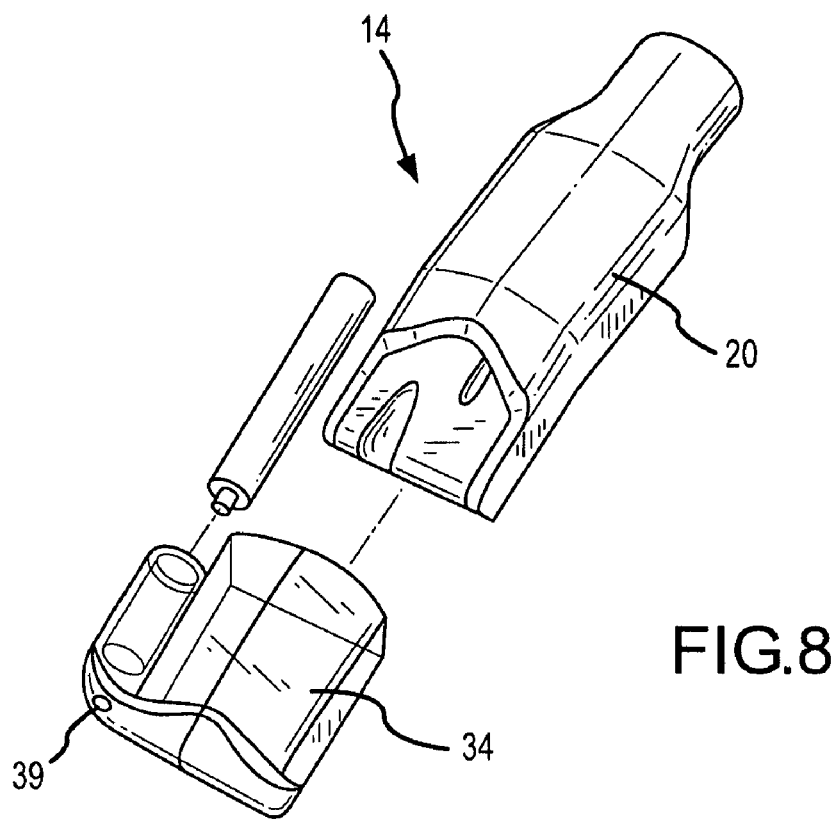
FIG. 8 is an exploded view of the distal end of an ablation and visualization device and a transparent cap.

FIG. 8 illustrates an embodiment of device 10 wherein distal end 14 is configured to receive a transparent cap 34. Cap 34 provides a mechanism, for example an opening 36, for coupling scope 28 to distal end 14 of device 10. The use of cap 34 facilitates rapid and simple coupling and decoupling of scope 28. This provides the physician with the option of utilizing device 10 either with or without scope 28 depending, for example, on whether a minimally invasive procedure is used. Cap 34 also provides the physician the option of adding scope 28 to device 10 during the ablation procedure.

Figure 12:
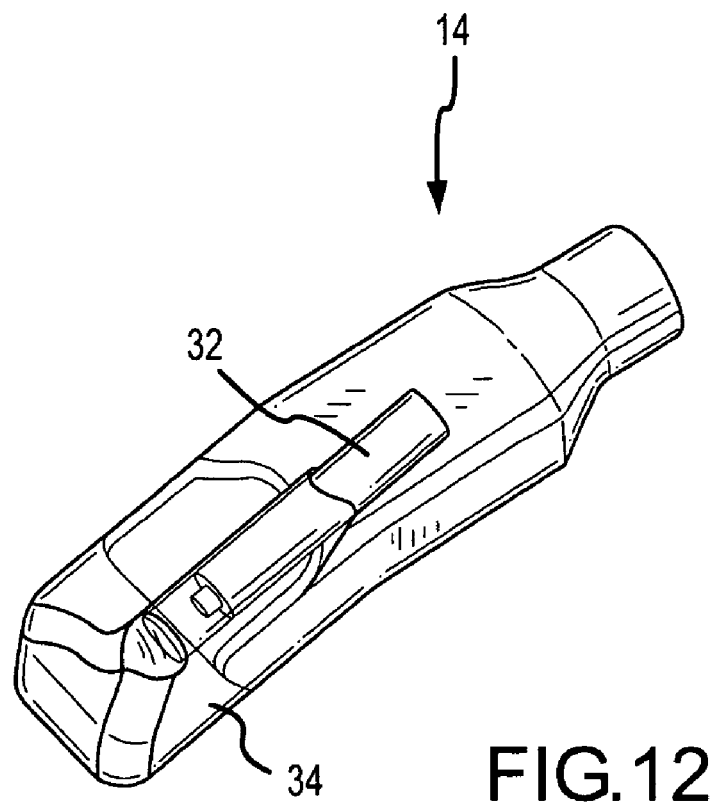
FIG. 12 is an isometric view of the distal end of an ablation and visualization device utilizing a transparent cap to couple the scope in an orthogonal position.
Figure 13:
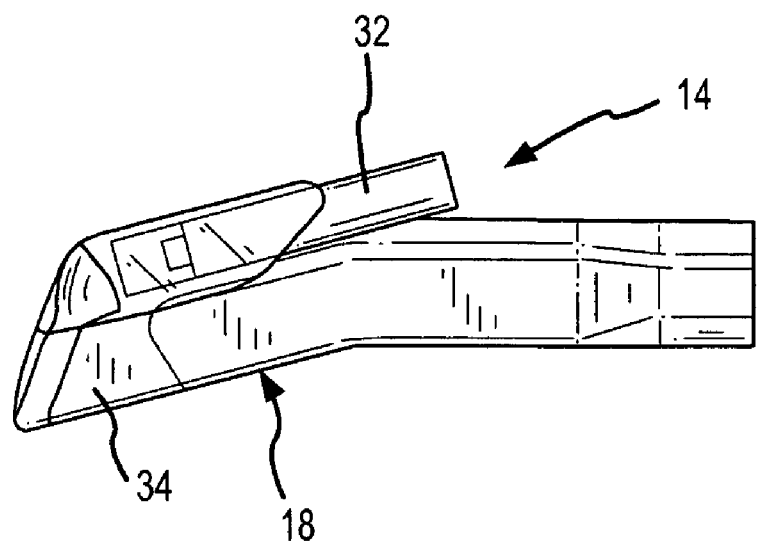
FIG. 13 is a side view of FIG. 12.
Figure 14:
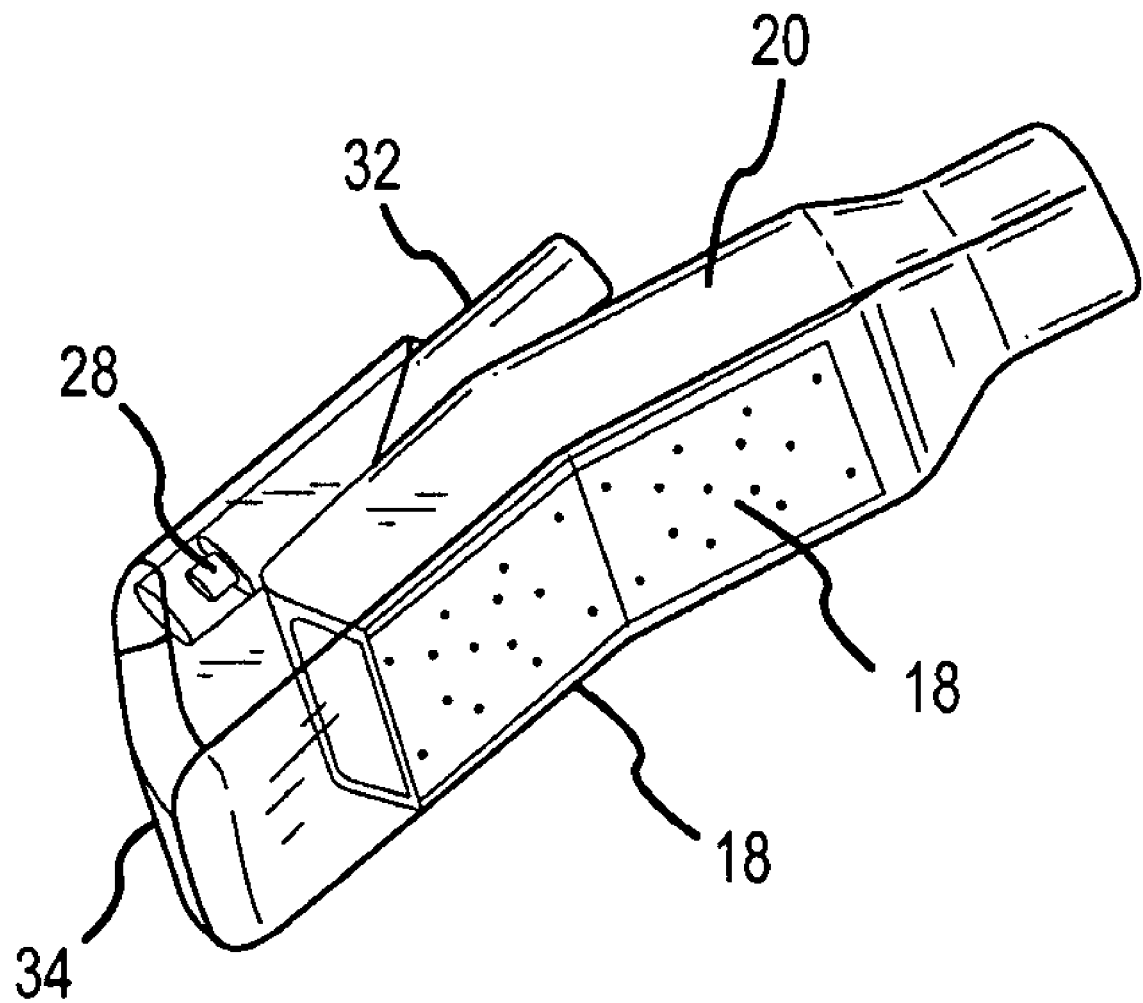
FIG. 14 is an isometric bottom view of FIG. 12.

Further, cap 34 is designed and intended to be easily attached to and removed from distal end 14 of device 10. As shown in FIGS. 9-14, a variety of different caps 34 may be utilized depending on the desired position of scope 28 relative to ablation elements 18. For example, one cap 34 may be configured to position scope 28 laterally relative to ablation elements 18 (FIGS. 9-11), while a second cap 34 may be configured to position scope 28 orthogonally relative to ablation elements 18 (FIGS. 12-14). Thus, the physician has the flexibility to choose a particular configuration of scope 28 relative to ablation elements 18 prior to starting an ablation procedure, and to alter that configuration during the procedure if so desired.

Cap 34 may also extend distally beyond ablation elements 18 if such a view is desired. The resultant additional transparent space in front of scope 28 may provide the physician with additional perspective on other anatomical bodies near the target tissue, for example by displacing blood that would otherwise obscure the view of scope 28. Cap 34 further protects aperture 30 from coming into contact with material that could attach to, obstruct, or damage scope 28. Alternatively, an overhang 37 on scope 28, such as that illustrated in FIG. 2, may protect aperture 30.

Figure 9:
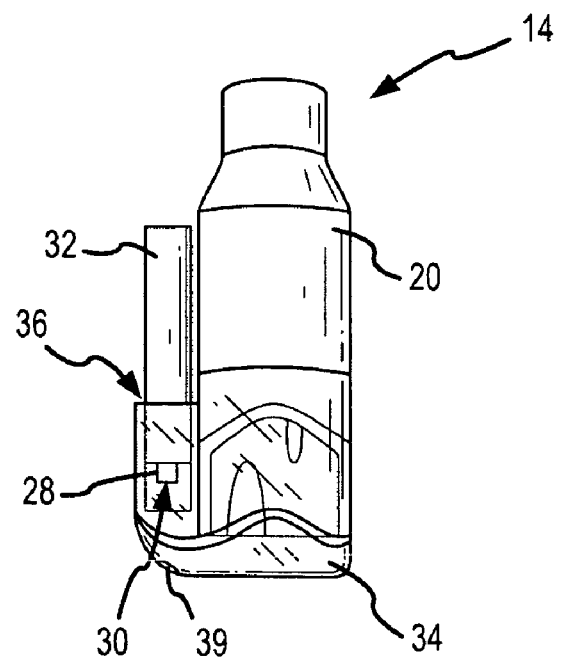
FIG. 9 is a top view of the distal end of an ablation and visualization device with a transparent cap that couples the scope in a lateral position.
Figure 10:
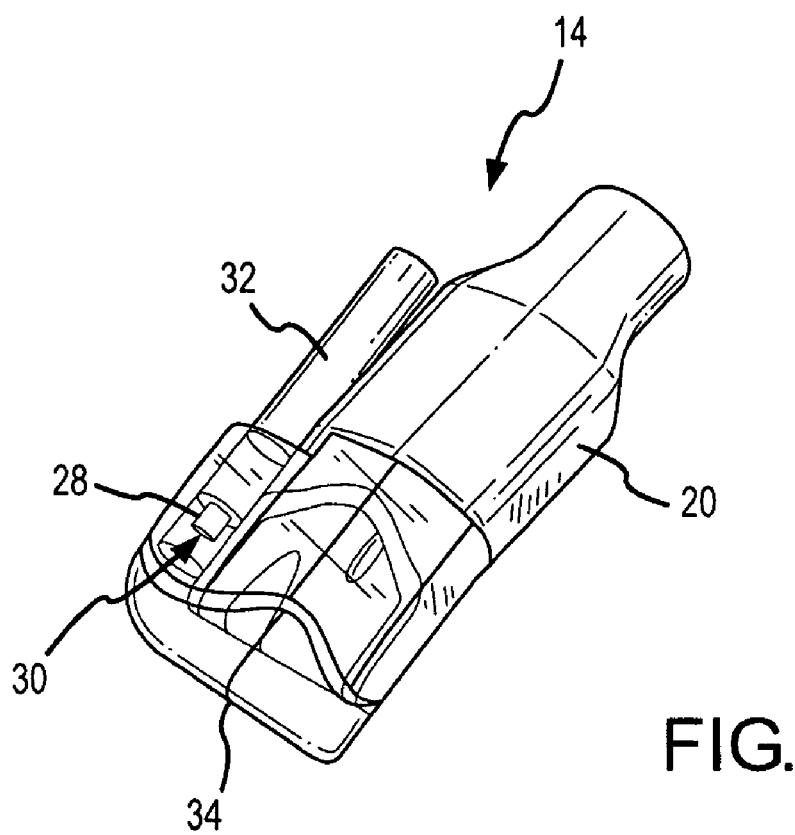
FIG. 10 is an isometric view of FIG. 9.
Figure 11:
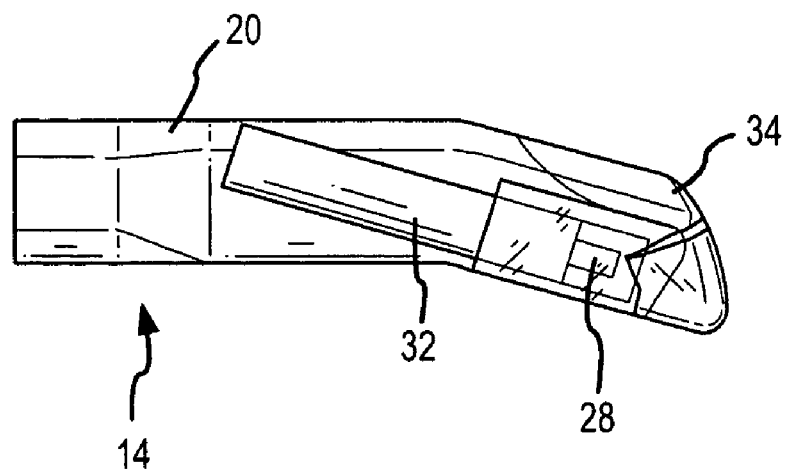
FIG. 11 is a side view of FIG. 9.

Device 10 may also include an optical element 39, such as a lens or filter, in order to narrow, broaden, filter, or otherwise alter the field of view or image captured by scope 28. For example, a fisheye lens could be utilized to increase the field of view of scope 28. Alternatively, a movable mirror could be utilized to alter the field of view of scope 28, effectively emulating the movable aperture 30 embodiment of FIG. 7. Optionally, one or more optical elements 39 are incorporated into cap 34, as shown in FIGS. 8 and 9.

Ablation and visualization device 10 may be used to create a mitral isthmus ablation lesion that is contiguous with a PV isolation ablation lesion. Device 10 is passed through an incision and into the patient. Device 10 may be introduced with scope 28 already attached thereto, or scope 28 may be attached to distal end 14 after introduction.

The imagery captured and collected by scope 28 is output on a display. If desired, the physician may move aperture 30 to change the field of view of scope 28. The physician utilizes the visual information output on the display to navigate device 10 within the patient and to properly position ablation elements 18 on the epicardial surface of the patient's heart to create the mitral isthmus ablation while avoiding nearby anatomical structures and non-target tissues. The physician may also utilize the display to ensure that ablation elements 18 are positioned to create a mitral isthmus ablation lesion that is contiguous with the PV isolation ablation lesion. The PV isolation ablation lesion may be created through the use of a belt-type ablation device that wraps around the pulmonary veins, such as that disclosed in U.S. Pat. No. 7,052,493, which is hereby incorporated by reference in its entirety as though fully set forth herein. One of ordinary skill in the art will appreciate, however, that any suitable device may be utilized to create the PV isolation ablation lesion.

Once properly positioned, the physician can then activate ablation elements 18 to deliver ablation energy to the cardiac tissue, and can utilize the display to maintain device 10 in the proper position on the beating heart during the procedure. The display may also be used to visually confirm complete ablation at the conclusion of the procedure.

Ablation elements 18 preferably deliver ultrasound energy focused in at least one dimension. In particular, ablation elements 18 preferably deliver focused ultrasound having a focal length of about 2 mm to about 20 mm, more preferably of about 2 mm to about 12 mm, and most preferably of about 8 mm. Stated another way, a focus is spaced apart from a bottom (or contact) surface of device 10 along a focal axis (FA) within the stated ranges. The focused ultrasound also forms an angle of about 10 degrees to about 170 degrees, more preferably of about 30 degrees to about 90 degrees, and most preferably of about 60 degrees relative to the FA. Preferably, a piezoelectric transducer is utilized. The transducer is preferably mounted within a housing having an enclosure and a top that fits over the enclosure. The enclosure may have curved lips on both sides of the enclosure that generally conform to the curvature of the transducer. The transducer preferably has a length of about 0.43 inch, a width of about 0.35 inch, and a thickness of about 0.017 inch. The transducer has a radius of curvature (R) consistent with the preferred focal lengths described above. The transducer forms an angle (A) with the focus (F) within the preferred angle ranges described above.

An advantage of using focused ultrasonic energy is that the energy can be concentrated within the tissue. Another advantage of using focused ultrasound is that the energy diverges after reaching the focus, thereby reducing the possibility of damaging tissue beyond the target tissue as compared to collimated ultrasonic energy. When ablating epicardial tissue with collimated ultrasound, the collimated ultrasound energy not absorbed by the target tissue travels through the heart chamber and remains concentrated on a relatively small area when it reaches the endocardial surface on the other side of the chamber. The present invention reduces the likelihood of damage to other structures since the ultrasonic energy diverges beyond the focus and is spread over a larger area.

Although the focused ultrasonic energy is preferably produced with a curved transducer, the focused ultrasonic energy may be produced with any suitable structure. For example, acoustic lensing may be used to provide focused ultrasound. The acoustic lens can be used with a flat piezoelectric element and matching layer. Furthermore, although the ultrasound energy is preferably emitted directly toward the tissue, the ultrasound energy may also be reflected off a surface and directed toward the tissue without departing from the scope of the invention.

The energy may also be produced by a number of small transducers oriented to focus or concentrate ultrasonic energy, such as at least about 90% of the energy, within the preferred angle ranges and radius of curvature described herein when viewed along a longitudinal axis or along the FA. For example, a multi-element acoustic phased array may be used to provide an acoustic beam-steering capability from one or more cells. One skilled in the art can also appreciate the use of multiple matching layers, focusing acoustic lenses, and non-focusing acoustic windows and the like. Thus, the focused energy may be produced in a number of different ways, including other ways not mentioned here, without departing from the scope of the invention.

In another aspect of the invention, device 10 is operated during two different time periods while varying at least one characteristic of device 10, such as the frequency of the ablating energy, the power of the ablating energy, the position of the focus relative to the tissue, and/or the ablating time. For example, device 10 may be operated at varying frequencies over time to ablate tissue in a controlled manner. Specifically, device 10 is preferably operated to create a transmural lesion by controlling the delivery of energy to the tissue. Although it is preferred to vary the frequency when ablating the tissue, device 10 may, of course, be operated at a single frequency without departing from the spirit and scope of the invention.

In a first treatment method of the present invention, the transducer is activated at a frequency of about 2 MHz to about 7 MHz, and preferably of about 3.5 MHz, and a power of about 80 watts to about 150 watts, and preferably of about 130 watts, in short bursts. For example, the transducer may be activated for about 0.01 second to about 2.0 seconds, and preferably for about 1.2 seconds. The transducer is inactive for about 2 seconds to about 90 seconds, more preferably about 5 seconds to about 80 seconds, and most preferably about 45 seconds between activations. In this manner, a controlled amount of accumulated energy can be delivered to the tissue in short bursts to heat tissue at and near the focus while minimizing the impact of blood cooling at the far surface. Ablation at this frequency may continue until a controlled amount of energy is delivered, such as about 0.5 kilojoule to about 3 kilojoules. Treatment at this frequency in relatively short bursts produces localized heating at the focus. At the first frequency, energy is not absorbed as quickly in the tissue as it is at higher frequencies, so that heating at the focus is not significantly affected by absorption of ultrasound energy in tissue before reaching the focus.

Following treatment at the first frequency, the transducer is operated for longer periods of time, preferably about 1 second to about 4 seconds, and more preferably about 2 seconds, to ablate tissue between the focus and the transducer. The frequency during this treatment is also preferably about 2 MHz to about 14 MHz, more preferably about 3 MHz to about 7 MHz, and most preferably about 6 MHz. The transducer is operated for about 0.7 second to about 4 seconds at a power of about 20 watts to about 80 watts, and preferably about 60 watts. The transducer is inactive for between about 3 seconds and about 60 seconds, and preferably for about 40 seconds, between each activation. In this manner, a controlled amount of energy can be delivered to heat tissue between the focus and the transducer. The treatment at this frequency may continue until a controlled amount of total energy is delivered, such as about 750 joules.

As a final treatment, the ultrasonic transducer is activated at a higher frequency to heat and ablate the near surface. The transducer is preferably operated at a frequency of between about 3 MHz and about 16 MHz, and preferably at about 6 MHz. The transducer is operated at lower power than the treatment methods above since the ultrasonic energy is rapidly absorbed by the tissue at these frequencies, so that the near surface is heated quickly. In a preferred method, the transducer is operated at about 2 watts to about 20 watts, and more preferably about 15 watts. The transducer is preferably operated for a sufficient duration to ablate tissue, such as about 20 seconds to about 80 seconds, and preferably about 40 seconds. Often, the near surface temperature will reach about 70 degrees C. to about 85 degrees C.

Each of the treatments described above may be used by itself or in combination with other treatments. Furthermore, the combination of transducer size, power, frequency, activation time, and focal length may all be varied to produce the desired delivery of ultrasound energy to the tissue. As such, it is understood that the preferred embodiment may be adjusted by adjusting one or more of the characteristics and, thus, these parameters may be changed without departing from the spirit and scope of the invention. The treatment sequence described above generally delivers energy closer to the near surface during the second treatment and even closer to the near surface for the third treatment (that is, it ablates tissue from the far surface towards the near surface in successive treatments).

The focus of the ultrasound energy may also be moved relative to the tissue to deliver energy to different depths in the tissue. The focus may be moved while ablation elements 18 are activated or may be moved between activations of ablation elements 18. Moving the focus of the ultrasound energy may be sufficient to create a transmural lesion without changing frequencies, or may be used in conjunction with a change in frequencies as described above. The focus may also be moved in any other manner such as with a phased array or variable acoustic lensing.

Although several embodiments of this invention have been described above with a certain degree of particularity, those skilled in the art could make numerous alterations to the disclosed embodiments without departing from the spirit or scope of this invention. For example, though FIG. 6 depicts scope 28 positioned distally relative to ablation elements 18, one of skill in the art will appreciate that scope 28 could equally well be positioned proximally relative to ablation elements 18 (i.e., closer to handle 24). Further, one of skill in the art will appreciate that the various features described in connection with individual embodiments may be combined, for example by providing a scope 28 with multiple articulated apertures 30 positioned distally relative to ablation elements 18, or by providing a single laterally positioned scope 28 on either side of ablation elements 18.

In addition, though the present device has been described in connection with visualizing target tissue in the treatment of atrial fibrillation, and in particular in the creation of a mitral isthmus ablation, it should be understood that the devices and methods disclosed herein are equally useful for visualizing target tissues in other ablation procedures. For example, rather than creating a mitral isthmus ablation lesion, the device disclosed herein may be used to fill in gaps in a PV isolation ablation lesion. The device may also be employed in the treatment of other electrophysiological conditions.

All directional references (e.g., upper, lower, upward, downward, left, right, leftward, rightward, top, bottom, above, below, vertical, horizontal, clockwise, and counter-clockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A device for ablating tissue, comprising:
a shaft having a distal segment articulable into a variety of positions relative to a remainder of the shaft and including a one dimensional array of two or more ablation elements, wherein the two or more ablation elements of the array are arranged on a common axis that is substantially parallel to a longitudinal axis of the shaft; and
a scope coupled to an exterior of said shaft proximate said distal segment, said scope including at least one image collecting aperture oriented to have a field of view looking along the longitudinal axis of the shaft.

2. The device according to claim 1, wherein said scope is positioned laterally relative to the array of two or more ablation elements.

3. The device according to claim 1, wherein said scope is positioned in a plane substantially parallel to and spaced apart from a plane in which the array of two or more ablation elements is located.

4. The device according to claim 1, wherein said scope is coupled to said shaft with said at least one aperture positioned proximally relative to the array of two or more ablation elements.

5. The device according to claim 1, wherein said scope is coupled to said shaft with said at least one aperture positioned distally relative to the array of two or more ablation elements.

6. The device according to claim 1, wherein said scope is coupled to said shaft such that the field of view of said scope includes at least a portion of the array of two or more ablation elements.

7. The device according to claim 1, wherein said scope is slidably coupled to said shaft via a collar, such that said scope can be positioned at two or more locations along said shaft.

8. The device according to claim 1, wherein said scope is rotatably coupled to said shaft via a collar, such that said scope can be positioned in a plurality of planes substantially parallel to and spaced apart from a plane in which the array of two or more ablation elements is located.

9. The device according to claim 1, wherein said scope is integrated with said shaft.

10. The device according to claim 1, wherein said scope includes a plurality of image collecting apertures.

11. The device according to claim 1, wherein said image collecting aperture comprises a movable image collecting aperture.

12. The device according to claim 1, further comprising a cap coupled to said distal segment of said shaft, wherein said scope is coupled to said shaft via said cap.

13. The device according to claim 12, wherein said scope is removably coupled to said cap.

14. The device according to claim 12, wherein said cap is removably coupled to said distal segment of said shaft.

15. The device according to claim 12, wherein said cap is substantially transparent.

16. The device according to claim 12, wherein said cap comprises at least one optical element positioned over said at least one image collecting aperture of said scope.

17. The device according to claim 1, further comprising at least one optical element positioned over said at least one image collecting aperture of said scope.

18. The device according to claim 1, wherein said scope comprises a fiber optic endoscope.

19. The device according to claim 1, wherein said scope comprises an infrared sensor.

20. The device according to claim 1, wherein said scope comprises an ultrasound sensor.

21. The device according to claim 1, wherein said scope is coupled to an output device configured to visually display imagery collected by said scope through said image collecting aperture.

22. The device according to claim 1, wherein the articulable distal segment is configured such that it retains a deformed shape when deformed by a user.

23. The device according to claim 22, wherein the articulable distal segment comprises a stacked coil.

24. The device according to claim 1, wherein the scope is coupled to the exterior of the shaft such that, when the distal segment of the shaft is articulated, the scope moves in unison therewith.

25. An ablation and visualization device, comprising:
a shaft having a distal segment articulable into a variety of positions relative to a remainder of the shaft and including at least two ablation elements arranged on a common axis that is substantially parallel to a longitudinal axis of the shaft; and
a scope directly attached to an exterior surface of said distal segment of said shaft, said scope including at least one image collecting aperture,
wherein the image collecting aperture has a field of view looking along a direction in which the at least two ablation elements are arrayed.

26. The device according to claim 25, further comprising an optical element positioned over said image collecting aperture to alter a field of view of said scope.

27. The device according to claim 26, wherein said optical element comprises a lens.

28. The device according to claim 26, wherein said optical element comprises a filter.

29. The device according to claim 25, further comprising a substantially transparent cap coupled to said distal segment of said shaft, and wherein said scope is coupled to said cap.

30. The device according to claim 25, wherein said scope is integrated with said distal segment of said shaft.

31. The device according to claim 25, wherein said at least one image collecting aperture is movable via a swivel assembly.

32. A device for ablating tissue, comprising:
a shaft having a relatively rigid proximal segment and a plastically deformable distal segment;
a housing coupled to the plastically deformable distal segment and having an exterior surface;
at least one ablation element substantially enclosed within the housing; and
a scope having an exterior surface, the exterior surface of the scope being integrally and permanently attached to the exterior surface of the housing, said scope including at least one image collecting aperture.

* * * * *